(12) United States Patent
Hayman

(10) Patent No.: US 11,130,002 B1
(45) Date of Patent: Sep. 28, 2021

(54) ENCLOSURE APPARATUS FOR KIT SYSTEM FOR SKINCARE REJUVENATION

(71) Applicant: Hillary Hayman, Los Angeles, CA (US)

(72) Inventor: Hillary Hayman, Los Angeles, CA (US)

(73) Assignee: ELYSE ENTERPRISES LLC, Los Angeles, CA (US)

( * ) Notice: Subject to any disclaimer, the term of this patent is extended or adjusted under 35 U.S.C. 154(b) by 0 days.

(21) Appl. No.: 17/012,958

(22) Filed: Sep. 4, 2020

(51) Int. Cl.
| | | |
|---|---|---|
| A45C 5/00 | (2006.01) | |
| A61N 5/06 | (2006.01) | |
| A61M 37/00 | (2006.01) | |
| A45D 33/32 | (2006.01) | |
| A45D 40/18 | (2006.01) | |
| B65D 25/10 | (2006.01) | |
| B65D 43/18 | (2006.01) | |

(52) U.S. Cl.
CPC ............ *A61N 5/0616* (2013.01); *A45C 5/005* (2013.01); *A45C 2200/15* (2013.01); *A45D 33/32* (2013.01); *A45D 40/18* (2013.01); *A61M 37/00* (2013.01); *A61N 5/062* (2013.01); *A61N 2005/0626* (2013.01); *A61N 2005/0633* (2013.01); *A61N 2005/0663* (2013.01); *B65D 25/10* (2013.01); *B65D 43/18* (2013.01)

(58) Field of Classification Search
CPC .......... A45C 15/06; A45C 5/00; A45D 33/32; A45D 33/26; B65D 43/18; B42F 9/001–005
USPC ...... 206/45.26; 248/136, 150, 397, 456, 461
See application file for complete search history.

(56) References Cited

U.S. PATENT DOCUMENTS

| 1,488,282 A * | 3/1924 | Phillips .................. A45D 33/26 132/294 |
|---|---|---|
| 3,381,120 A | 4/1968 | Fleisher et al. |

(Continued)

FOREIGN PATENT DOCUMENTS

| DE | 870015 C * | 3/1953 | ............. A45D 33/26 |
|---|---|---|---|
| DE | 9416518 U1 * | 2/1996 | ............. A45C 15/04 |

(Continued)

OTHER PUBLICATIONS

International Search Report and Written Opinion for PCT/US2020/049625, dated Jan. 7, 2021.

*Primary Examiner* — Mollie Impink
(74) *Attorney, Agent, or Firm* — Concept IP LLP; Pejman Yedidsion

(57) ABSTRACT

An enclosure apparatus has a first wall, second wall, third wall, and fourth wall. The enclosure apparatus has a bottom portion operably attached to the first wall, second wall, third wall, and fourth wall. In addition, a support mechanism is operably attached to an exterior surface of the bottom portion. The enclosure apparatus also has a top portion operably attached to the first wall, the second wall, the third wall, and the fourth wall. Additionally, the enclosure apparatus has a swivel mechanism operably connected to a corner of the top portion and at least one of the first wall, second wall, third wall, and fourth wall. The top portion swivels to open and close the enclosure apparatus via the swivel mechanism. Finally, the enclosure apparatus has a lip mechanism operably attached to an edge of the top portion. The lip mechanism is configured to receive a mobile computing device.

20 Claims, 11 Drawing Sheets

(56) References Cited

U.S. PATENT DOCUMENTS

| | | | | |
|---|---|---|---|---|
| 4,555,128 A | * | 11/1985 | White | A47B 23/043 |
| | | | | 281/45 |
| 6,679,468 B1 | * | 1/2004 | Hsu | A45C 9/00 |
| | | | | 248/454 |
| 8,376,984 B2 | | 2/2013 | James | |
| 9,450,432 B1 | | 9/2016 | Burns | |
| 2004/0256534 A1 | | 12/2004 | Phifer et al. | |
| 2008/0011915 A1 | | 1/2008 | Landman | |
| 2009/0126758 A1 | * | 5/2009 | Chen | A45D 33/22 |
| | | | | 132/295 |
| 2010/0145255 A1 | * | 6/2010 | Popescu | A61K 31/197 |
| | | | | 604/20 |
| 2012/0210912 A1 | | 8/2012 | Florendo | |
| 2012/0279516 A1 | * | 11/2012 | Bouix | A45D 33/26 |
| | | | | 132/301 |
| 2013/0277237 A1 | * | 10/2013 | Wang | A45C 11/00 |
| | | | | 206/45.2 |
| 2014/0306587 A1 | | 10/2014 | Pun | |
| 2016/0198819 A1 | | 7/2016 | Grund et al. | |
| 2017/0024589 A1 | | 1/2017 | Schumacher et al. | |

FOREIGN PATENT DOCUMENTS

| | | | | |
|---|---|---|---|---|
| DE | 29500497 U1 | * | 5/1996 | F25D 11/00 |
| DE | 29508354 U1 | * | 9/1996 | A45C 5/005 |
| DE | 202013102228 U1 | * | 6/2013 | A45C 5/005 |
| FR | 2870691 A1 | * | 12/2005 | A45C 5/005 |
| KR | 20120092787 A | * | 8/2012 | |
| WO | 2015161799 A1 | | 10/2015 | |

* cited by examiner

ENCLOSURE APPARATUS FOR KIT SYSTEM FOR SKINCARE REJUVENATION

BACKGROUND

1. Field

This disclosure generally relates to enclosure apparatuses. More particularly, the disclosure relates to an enclosure apparatus for a kit system for mimicking plastic surgery results.

2. General Background

A plastic surgery procedure is typically performed in an office of a plastic surgeon, often at significant expense and inconvenience for those people wanting to improve the appearance of their skin. For instance, many people often have to travel far distances to obtain the services of a qualified plastic surgeon to perform the plastic surgery procedure. Although some people may elect to have a plastic surgery procedure (e.g., facelift, jaw lift, eye wrinkle reduction, etc.) to rejuvenate the appearance of their skin, others require plastic surgery to diminish or eliminate the effects (e.g., scar tissue, burns, etc.) from injuries. As a result, plastic surgery procedures are typically accessible only to a limited group, which may exclude those who need them most.

Accordingly, geographical limitations often limit the ability for some users, and particularly those who want them more out of necessity than aesthetic preference, to obtain the benefits of skincare rejuvenation procedures.

SUMMARY

In one embodiment, an enclosure apparatus has a first wall, second wall, third wall, and fourth wall. The enclosure apparatus has a bottom portion operably attached to the first wall, second wall, third wall, and fourth wall. In addition, a support mechanism is operably attached to an exterior surface of the bottom portion. The support mechanism is configured to extend outwardly away from the bottom portion to position the enclosure apparatus in an upright position. The enclosure apparatus also has a top portion operably attached to the first wall, the second wall, the third wall, and the fourth wall.

Additionally, the enclosure apparatus has a swivel mechanism operably connected to a corner of the top portion and at least one of the first wall, second wall, third wall, and fourth wall. The top portion swivels to open and close the enclosure apparatus via the swivel mechanism. Finally, the enclosure apparatus has a lip mechanism operably attached to an edge of the top portion. The lip mechanism is configured to receive a mobile computing device.

In another embodiment, the enclosure apparatus may have a power supply compartment within an interior portion of the enclosure apparatus. The power supply compartment stores a rechargeable power supply. Furthermore, the enclosure apparatus has a port for supplying power to the mobile computing device via a cable connected to the mobile computing device. The port is positioned on an exterior portion of the enclosure apparatus.

BRIEF DESCRIPTION OF THE DRAWINGS

The above-mentioned features of the present disclosure will become more apparent with reference to the following description taken in conjunction with the accompanying drawings wherein like reference numerals denote like elements and in which.

DETAILED DESCRIPTION

An enclosure apparatus is provided to allow manufacturers and distributers of a kit system for mimicking plastic surgery results to easily sell the kit system to customers as a single unit, and allow users to easily store the components of the kit system for subsequent usage. (Alternatively, the enclosure apparatus may be utilized to store components for a kit system that performs skincare rejuvenation without mimicking plastic surgery results.) The enclosure apparatus allows a user to store the components of the kit system for travel, thereby allowing users to have constant access to their skincare rejuvenation system without the need to go to a physical dermatology or plastic surgery office. Additionally, the enclosure apparatus allows for functional use of a software application (an "app") that may be utilized in conjunction with the kit system. In essence, the enclosure apparatus facilitates use of a mobile computing device to provide a user with guidance on use of the kit system during actual usage of the kit system.

For example, the kit system may have componentry, such as a derma roller, a chemical compound, and a red light therapy machine, directed toward a three-step process for skincare rejuvenation. (Other types of kit systems and processes may be used instead.) The enclosure apparatus has mechanical and electrical features that allow for integration of the mobile computing device (e.g., smartphone, tablet device, etc.) with the enclosure apparatus, thereby allowing the mobile computing device to execute the app for providing audiovisual instructions on use of the three-step process, as an example, with the componentry stored within the enclosure apparatus. As a result, the user is able to have an integrated apparatus for storing kit system components and enabling kit system instruction through a mobile computing device.

Figure 1A:
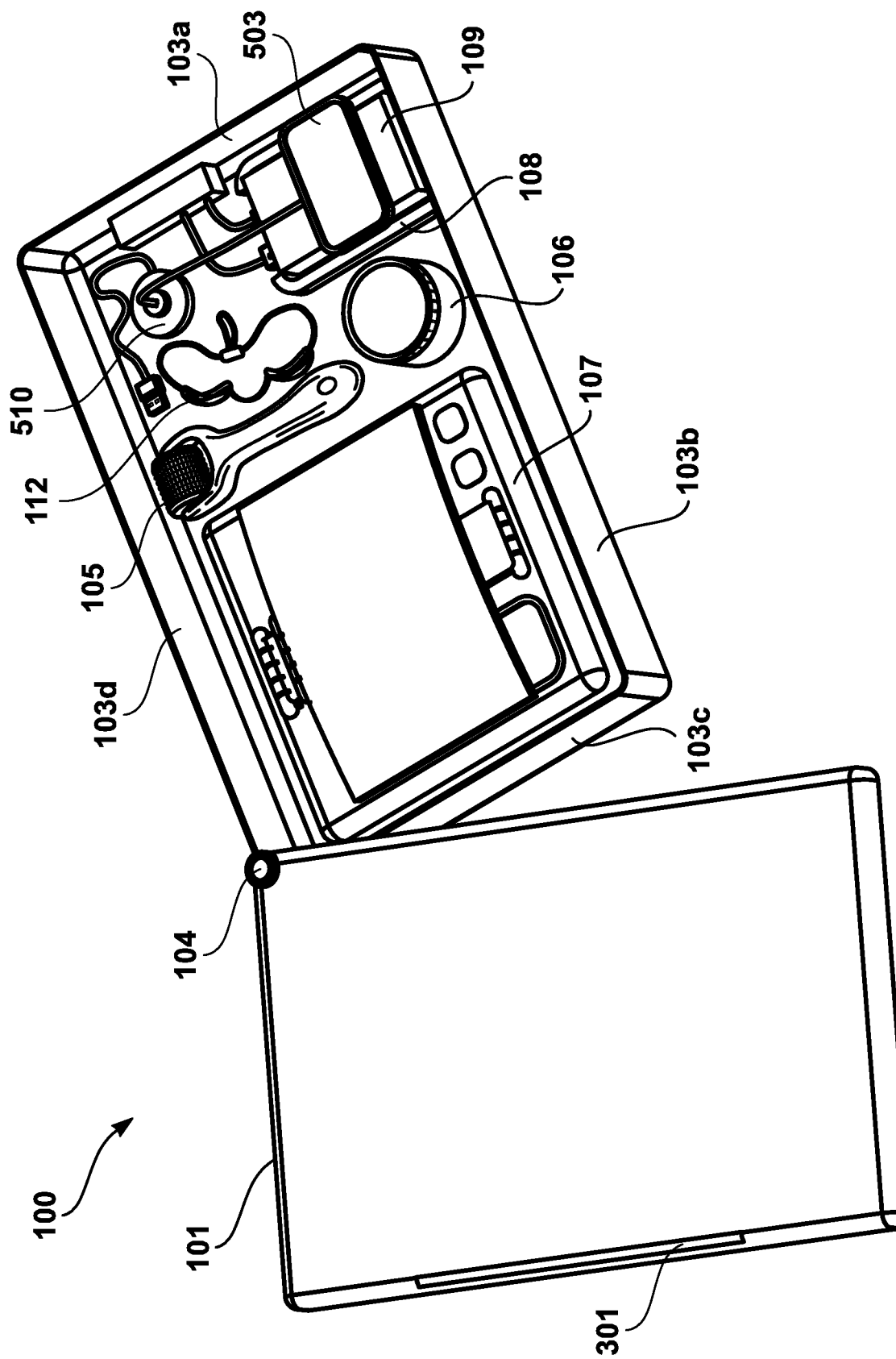
FIG. 1A illustrates an example of an enclosure apparatus that may be utilized to store kit system componentry, with all the componentry stored therein.
Figure 1B:
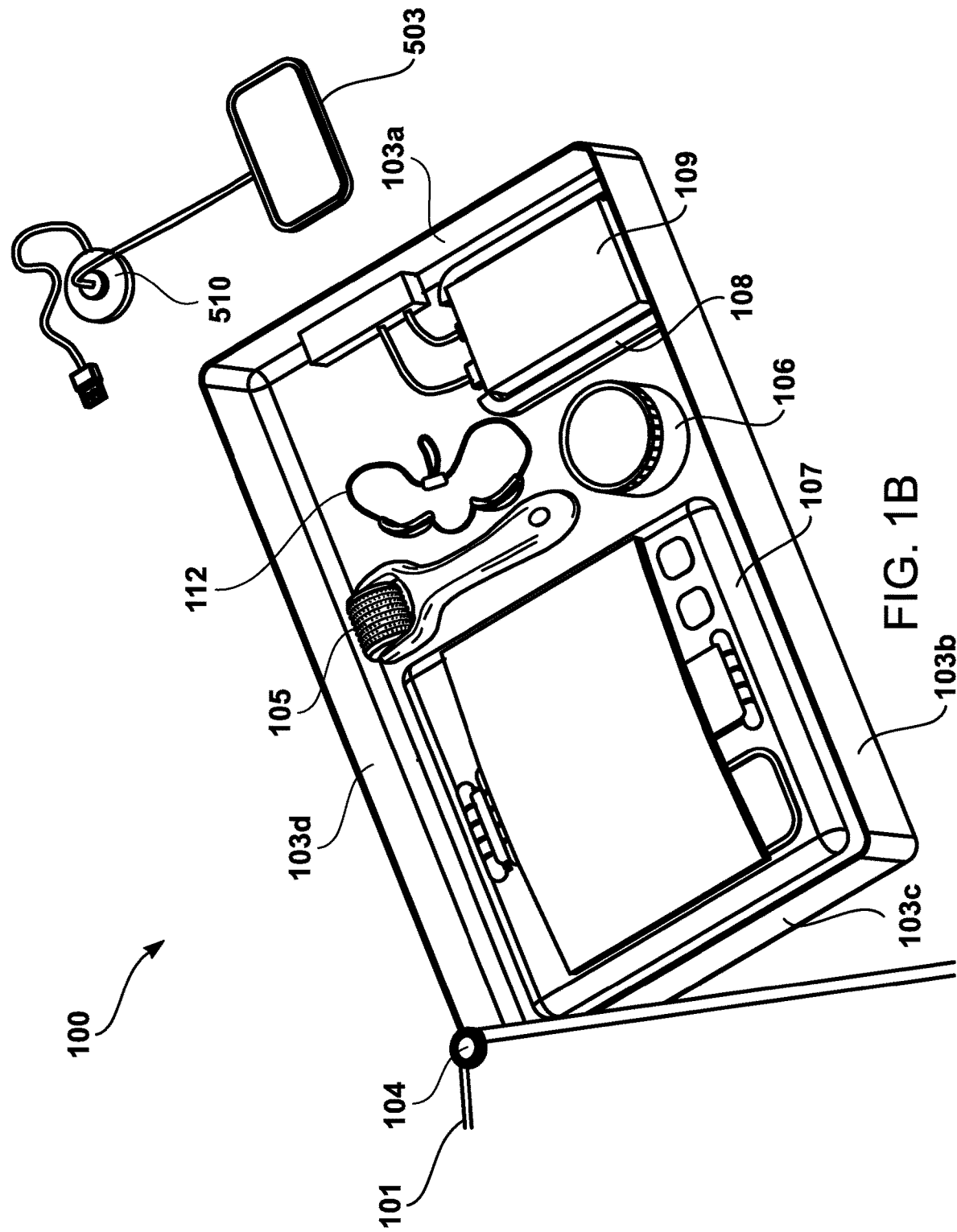
FIG. 1B illustrates the example of FIG. 1A with the lighting device removed from the enclosure apparatus.

FIGS. 1A and 1B illustrate an example of an enclosure apparatus 100 that may be utilized to store kit system componentry, for product shipping by a manufacturer/distributer as well as for subsequent storage by a user after each user of the kit system. In particular, FIG. 1A illustrates an example of the enclosure apparatus 100 being utilized to store kit system componentry, with all the componentry stored therein. The enclosure apparatus 100 has a top portion 101 that may be opened or closed with respect to a bottom portion 102 and one or more side walls 103a-d. As an example, the enclosure apparatus 100 is illustrated as having a rectangular configuration; however, the enclosure apparatus 100 may have different shapes (e.g., square, circle, oval, etc.) from that which is illustrated in FIG. 1. In one embodiment, the enclosure apparatus 100 has a swivel mechanism 104 that is utilized to open and close the top portion 101 with respect to the remainder of the enclosure apparatus 100. For example, the swivel mechanism may be positioned in a corner of the top portion 101 to engage with a receiving mechanism in one or more of the walls 103a-d. In essence, the top portion 101 may rotate with respect to the remainder of the enclosure apparatus 100 to open and close the enclosure apparatus 100.

The swivel mechanism 104 is provided as just one example of a mechanism to open and close the enclosure apparatus 100. As another example, a hinge mechanism may be utilized instead. Other types of mechanisms may be utilized to move the top portion 101 with respect to the remainder of the enclosure apparatus 100, and potentially in different ways than via a rotation. Furthermore, the enclosure mechanism does not have to be positioned at a corner; it may be positioned along one or more edges of the enclosure apparatus 100. Finally, although only one top portion 101 is illustrated for use with the enclosure apparatus 100, multiple top portions (e.g., two partitions via multiple swivels) may be utilized instead.

As an example, the enclosure apparatus 100 is illustrated as including various components, such as a derma roller 105, chemical compound container 106, and a red light therapy machine 107; these components may be utilized in conjunction with a three-step process that provides users with skincare rejuvenation that mimics plastic surgery results, without users having to undergo conventional plastic surgery procedures within a plastic surgeon's office. The three-step process has been discovered to yield results that were not readily predictable; such results mimic the effects of various plastic surgery procedures (e.g., facelifts, jaw lifts, neck lifts, forehead lifts, lower eyelid blepharoplasty, and the like) without a user having to undergo a plastic surgery procedure at the office of a medical practitioner. (Although the components corresponding to the three-step process are illustrated, different components may be stored by the enclosure apparatus 100 for other processes.) In essence, the three-step process includes application of various invasive and non-invasive devices/products according to particular parameters to mimic plastic surgery results. Firstly, the three-step process includes usage of the derma roller 105 in an area of intended rejuvenation. Particular needle lengths and movement of the derma roller 105 has been discovered to maximize skin rejuvenation. Secondly, a chemical compound containing vitamin $A_1$ (e.g., Retinol), positioned within the chemical compound container 106, is applied to the area of intended skin rejuvenation via the channels in the skin created by the derma roller 105. Accordingly, the chemical compound is able to reach the dermis layer of the skin, directly underneath the epidermis, much faster than would be required through prolonged exposure to the chemical compound; as a result, collagen production is increased in an optimal manner to rejuvenate (i.e., tone, tighten, and/or lift) the skin. Finally, the red light therapy device 107 is utilized to emit red light (i.e., light having a wavelength of six hundred ten nanometers to seven hundred nanometers) toward the area of intended rejuvenation, which further increases collagen production. Various other types and quantities of components may be utilized other than those illustrated in this example. For instance, a different type of chemical compound other than Retinol may be utilized, or a blue light therapy device may be utilized instead of the red light therapy device 107.

In one embodiment, the internal section of the enclosure apparatus 100 is form fitted to accommodate the particular components situated therein. For instance, the internal section may be molded to correspond to the specific shapes of the components. Alternatively, the internal section may not have any form fitting.

In one embodiment, the internal compartment of the enclosure apparatus may have a power supply compartment 108 that encloses a power supply 109 (e.g., lithium ion battery), which may be rechargeable. The power supply 109 may be operably connected to one or more ports (e.g., USB) that are accessible from the exterior of the enclosure apparatus 100. Accordingly, a mobile computing device may be plugged into a port to be charged via the power supply 109. Additionally, the power supply 109 may be connected to a port that allows for connection to an A/C power outlet for recharging of the power supply 109. The power supply 109 may also be removable from the enclosure apparatus 100, thereby allowing for external charging of the power supply 109. Alternatively, the power supply 109 may be irremovable from the enclosure apparatus 100.

Various additional components may be included within the enclosure apparatus 100. For example, a pair of safety goggles 112 may be stored for use with the red light therapy machine 107. Additionally, a lighting device 503 with an attachable base 510 (e.g., magnetic, clip-based, etc.) may be stored within the enclosure apparatus 100. Furthermore, FIG. 1B illustrates the example of FIG. 1A with the lighting device removed from the enclosure apparatus.

Figure 2A:
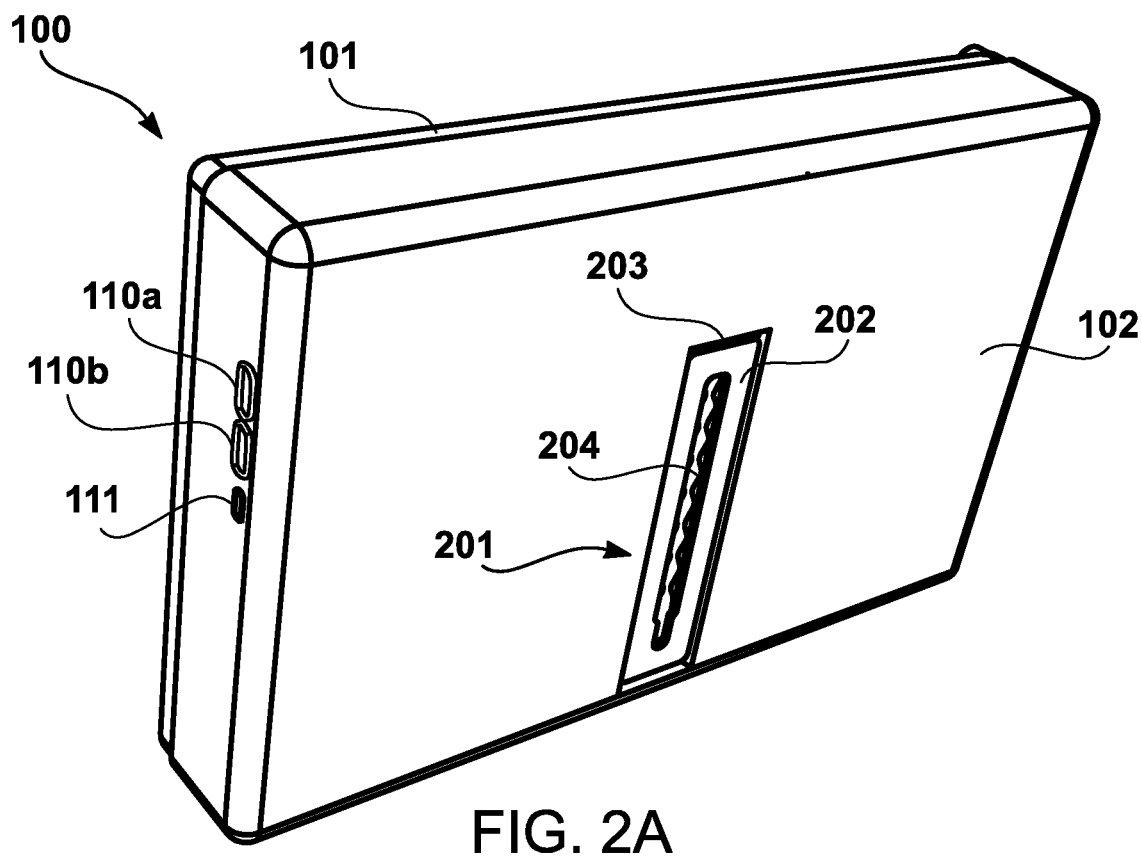
FIG. 2A illustrates the enclosure apparatus having the support mechanism in a retracted position.
Figure 2B:
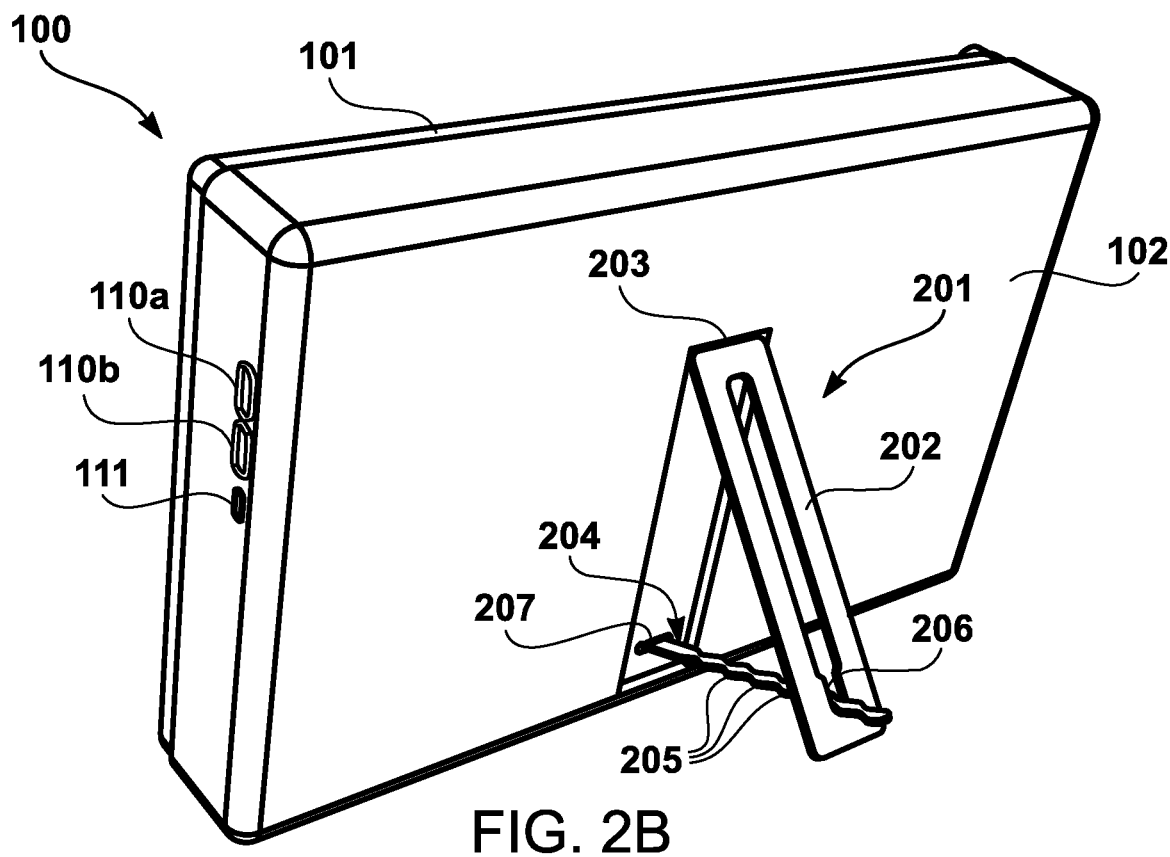
FIG. 2B illustrates the adjustment member being released for use.

Rather than being utilized as a conventional enclosure apparatus, which is typically discarded after opening, the enclosure apparatus 100 may be utilized by a user in a variety of functional ways subsequent to opening. For example, FIGS. 2A and 2B illustrate a support mechanism 201 that is adhered to the bottom portion 102. The support mechanism 201 may be utilized to place the enclosure apparatus 100 in an upright position so that the user may view the top portion 101 from a forward-looking viewpoint. In particular, FIG. 2A illustrates the enclosure apparatus 100 having the support mechanism 201 in a retracted position. As an example, the support mechanism 201 may have a support member 202 that is operably attached to one or more hinges 203, which are operably attached to the bottom portion 102. In one embodiment, as illustrated, the one or more hinges 203 may be positioned above a midline of the bottom portion 102; in this instance, the support mechanism 201 may provide optimal support because the midline portion, or a portion that is within close proximity to the midline portion, evenly distributes the weight from the enclosure apparatus 100, which can help avoid toppling of the enclosure apparatus 100. Accordingly, the support mechanism 201 may be positioned in substantial proximity (e.g., within a deviation of two to three inches) to the midline of the bottom portion. In another embodiment, the support mechanism 201 may be in another area, such as the top or bottom, of the bottom portion 102.

Additionally, the support mechanism 201 may have an adjustment member 204, which allows the user to adjust the angle at which the enclosure apparatus 100 is positioned upright. After the support mechanism 201 is extended from the bottom portion 102 of the enclosure apparatus 100, the adjustment member 204 may also be released for use (e.g., via a hinge mechanism 207, a swivel, another type of connection mechanism, or possibly as an independent member that is connected or applied via pressure upon use with the enclosure apparatus 100), as illustrated in FIG. 2B. The adjustment member 204 may have a plurality of adjustment protrusions 205, each corresponding to a different positioning angle; conversely, the support mechanism 201 may have one or more cavities 206 to match the adjustment protrusions 205. As an example, the user may want to place the enclosure apparatus 100 at a forty-five degree angle, which may correspond to the second adjustment protrusion 205 out of the seven adjustment protrusions 205. (Use of seven adjustment protrusions 205 is provided only as an example. As little as one adjustment protrusion may be utilized, and more than seven may also be utilized.)

Figure 3A:
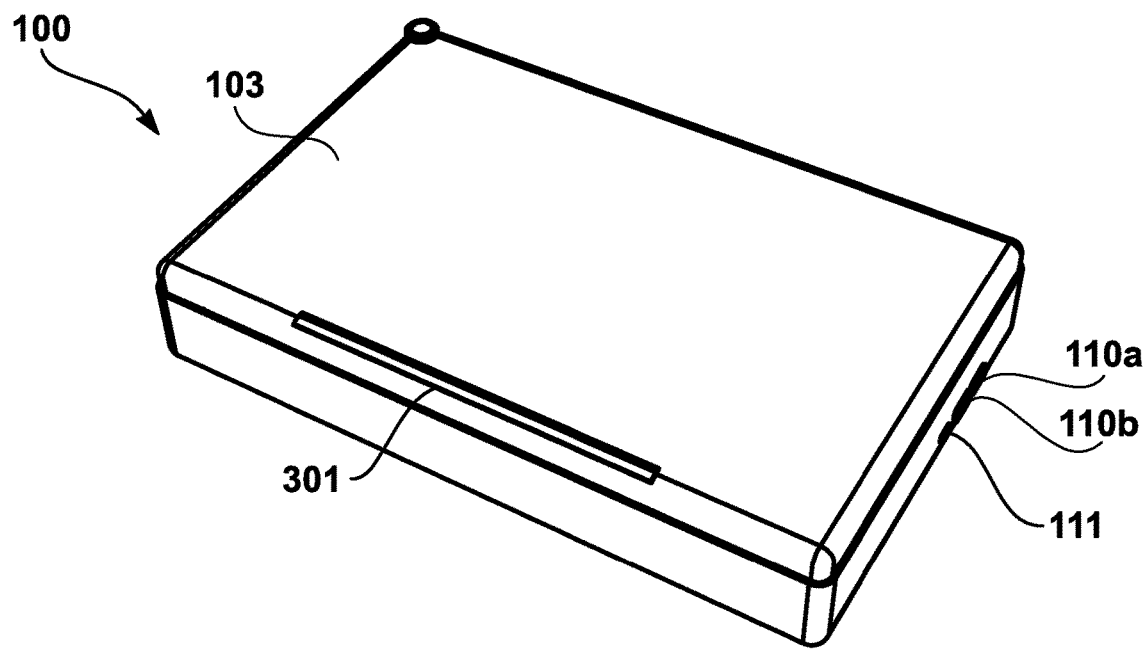
FIG. 3A illustrates the extendable/retractable lip being operably attached to an edge of the top portion.
Figure 3B:
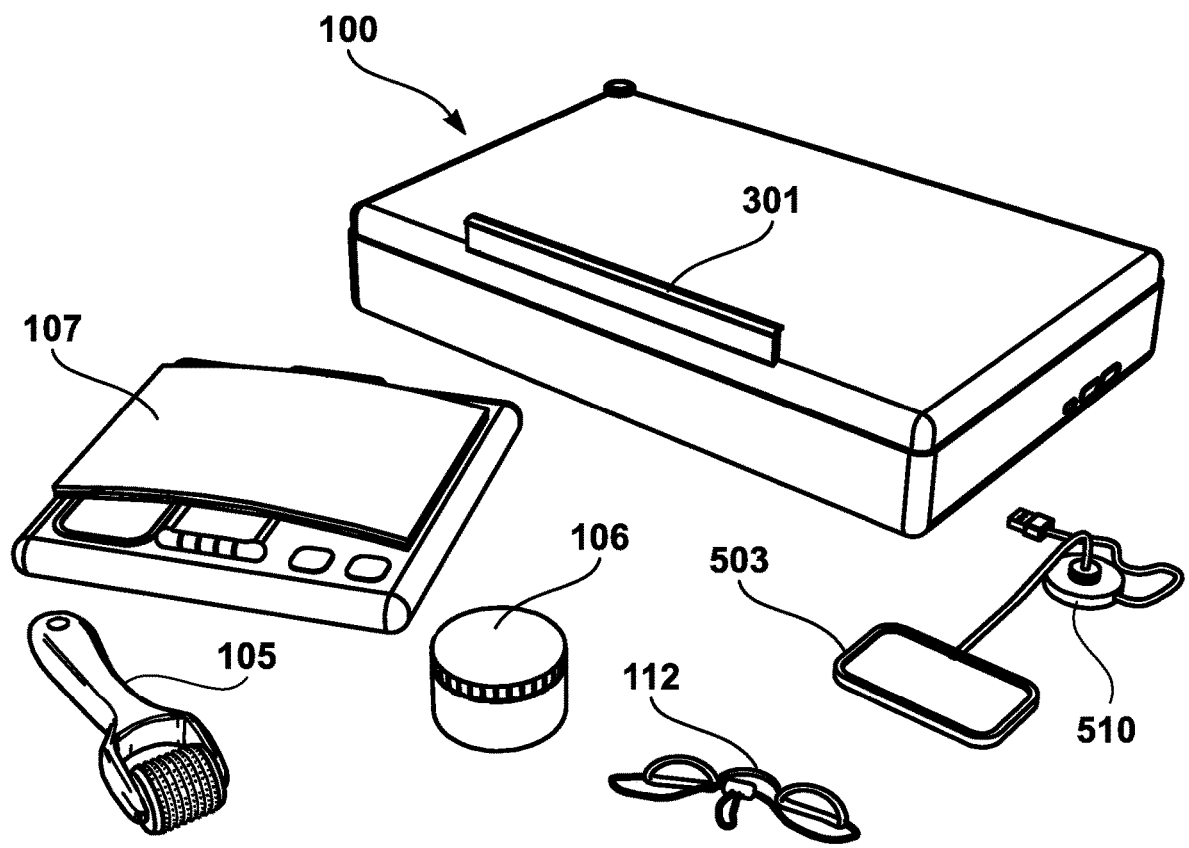
FIG. 3B illustrates the extendable/retractable lip in an extended state.

Subsequent to removal of the components, as illustrated in FIG. 1A, and positioning of the enclosure apparatus 100 in a particular upright position, as illustrated in FIGS. 2A and 2B, the user may configure the enclosure apparatus 100 for integration with a mobile computing device. In particular, the enclosure apparatus 100 may have an extendable/retractable lip 301, as illustrated in FIGS. 3A and 3B. In one embodiment, as illustrated in FIG. 3A, the extendable/retractable lip 301 is operably attached to an edge of the top portion 101. As a result, when the enclosure apparatus 100 is in an upright position, the extendable/retractable lip 301 is configured to face the user. In one embodiment, the edge of the top portion 101 that is utilized for the extendable/retractable lip 301 is parallel with the one or more hinges 203 positioned on the bottom portion 102, and is positioned at the same height or below the one or more hinges 203. As a result, the weight of extendable/retractable lip 301 is configured to bear the weight of a mobile computing device without any additional attachment mechanism. In another embodiment, the extendable/retractable lip 301 may be positioned on an edge perpendicular to the one or more hinges 203, but in this instance, the extendable/retractable lip 301 may utilize a connection mechanism (e.g., clip(s), magnet(s), etc.) to keep the mobile computing device in place. FIG. 3B illustrates the extendable/retractable lip 301 in an extended state.

Furthermore, the enclosure apparatus 100 may have multiple ports 110a and 110a (e.g., USB) to allow a computing device, the lighting device 503, or the red light therapy machine to be charged by the power supply 109. The enclosure apparatus 100 may also have a power supply port 111 to allow for recharging of the power supply 109.

Figure 4A:
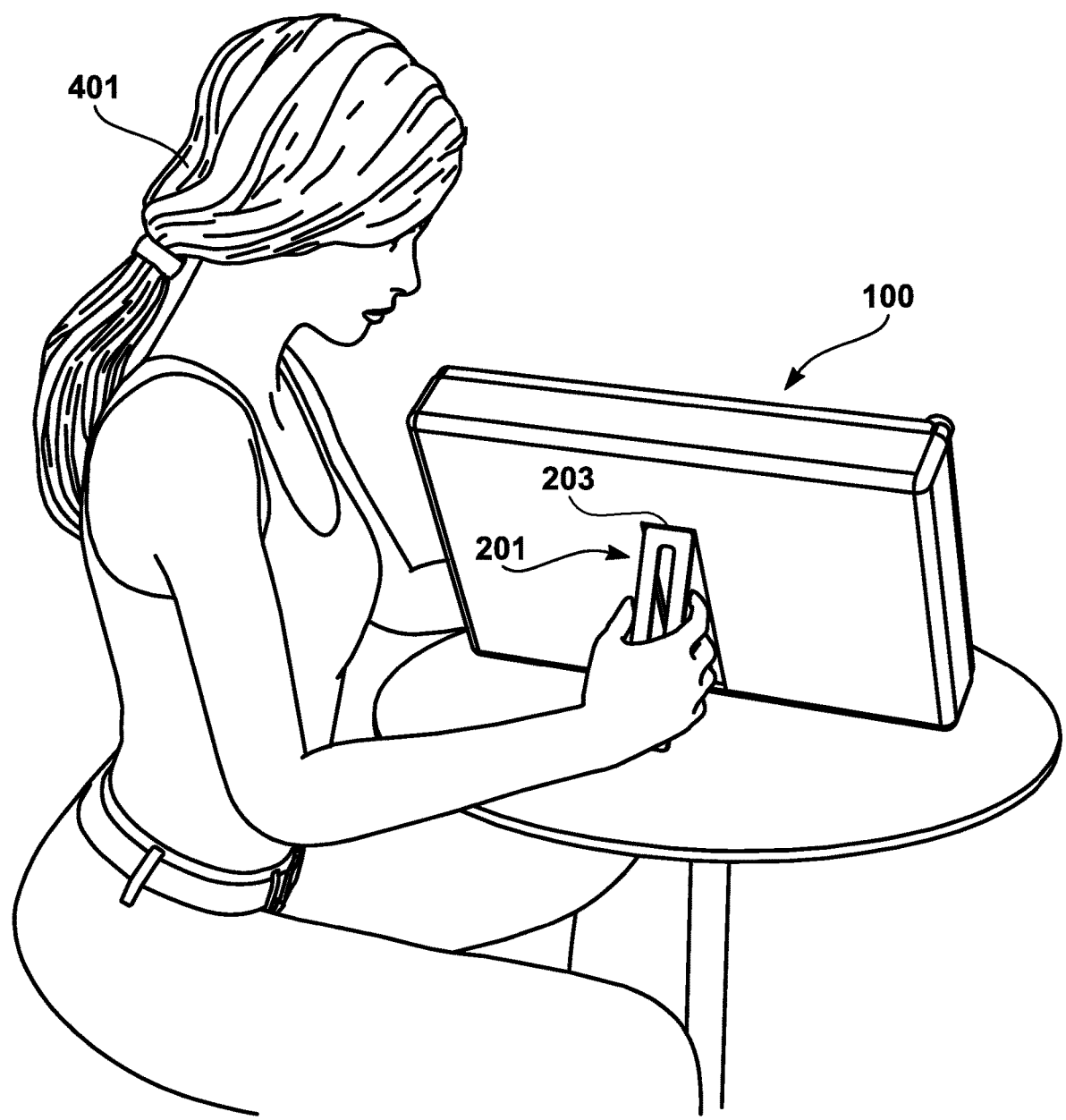
FIG. 4A illustrates the user extending the support mechanism.
Figure 4B:
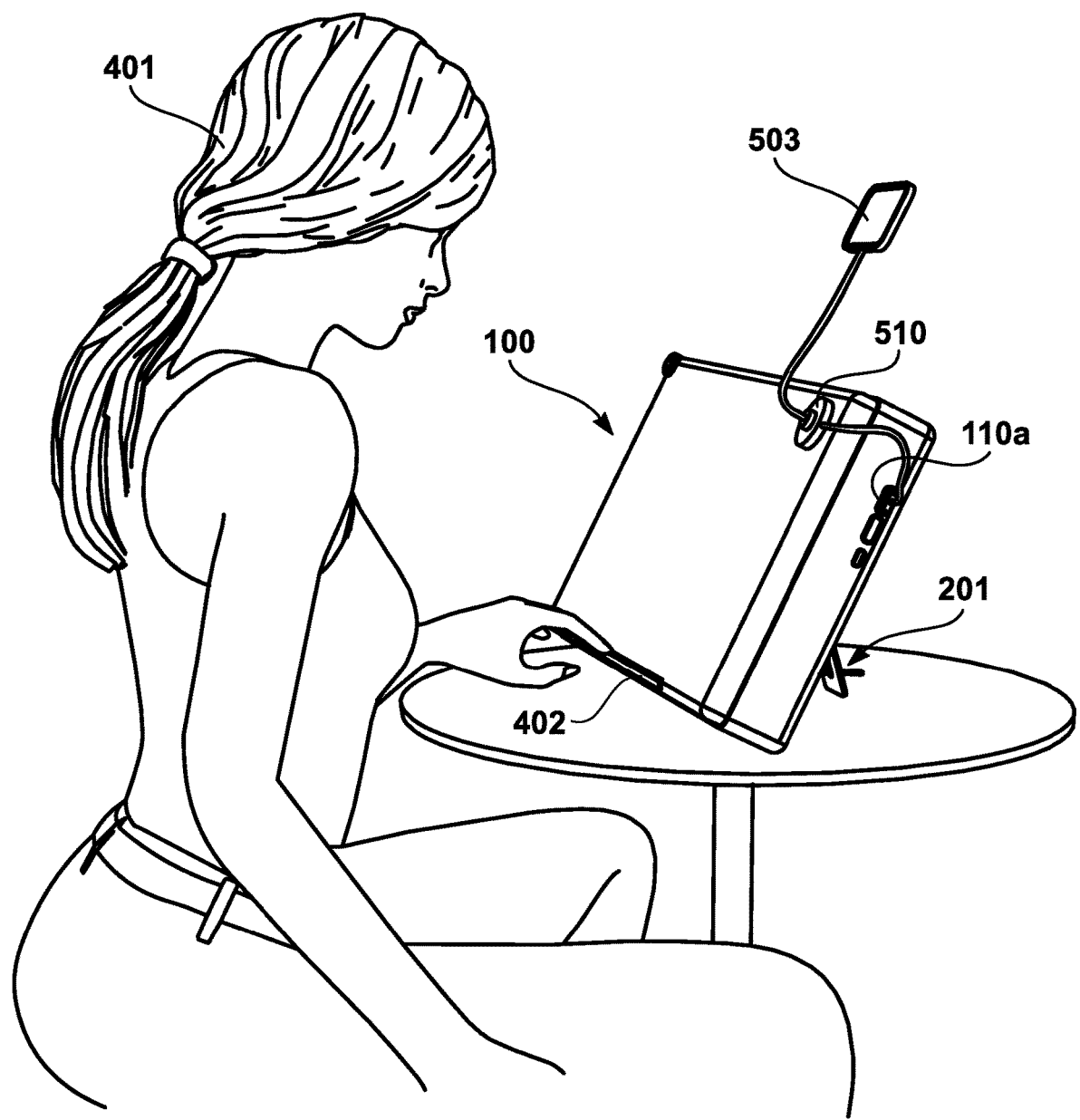
FIG. 4B illustrates the user placing his or her hand in proximity to the extendable/retractable lip when in the retracted state.
Figure 4C:
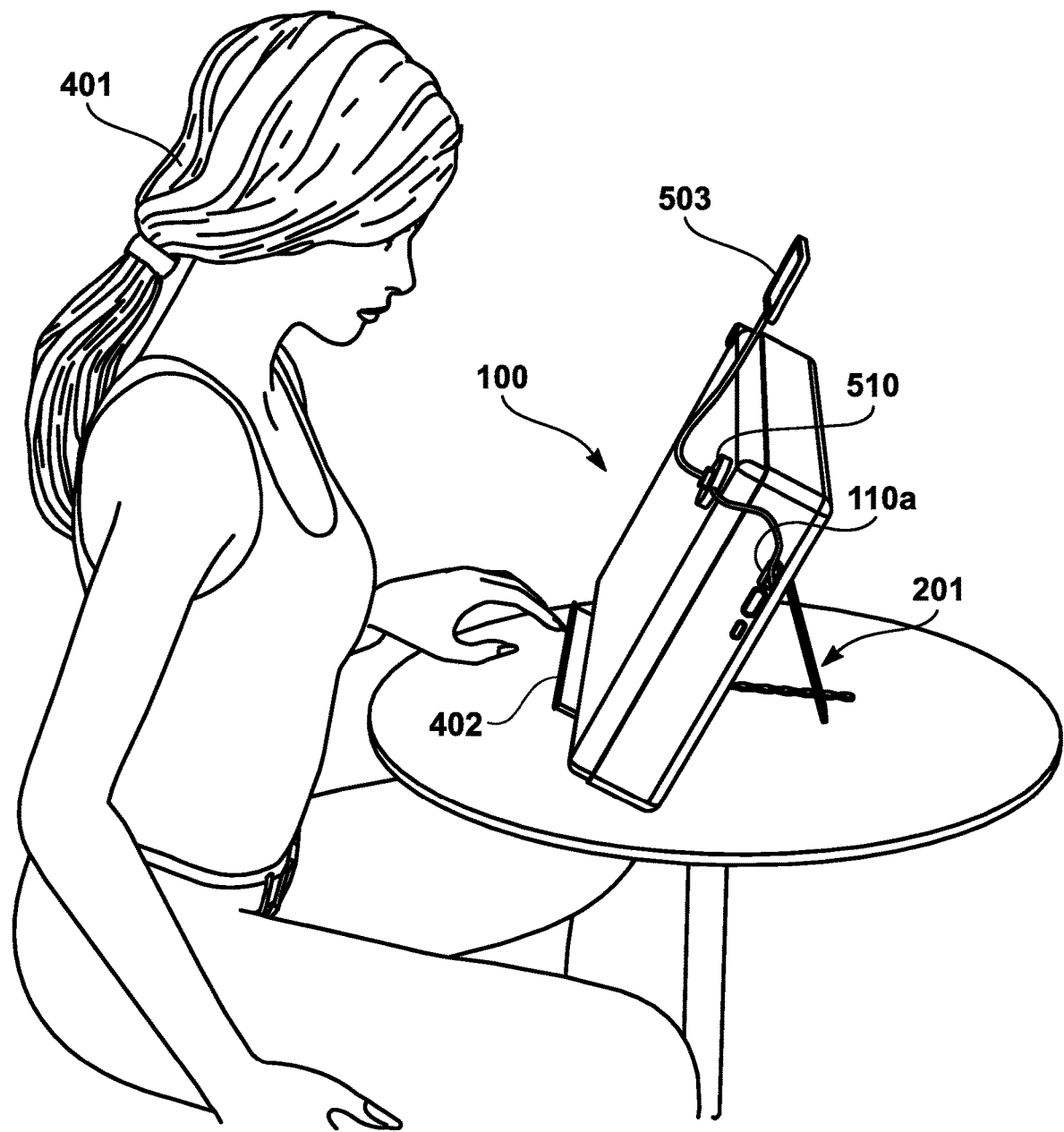
FIG. 4C illustrates the extendable/retractable lip in the extended state.

FIGS. 4A-4C illustrate a user 401 configuring the enclosure apparatus 100 for use. In particular, FIG. 4A illustrates the user 401 extending the support mechanism 201. Furthermore, the user 401 may place his or her hand in proximity to the extendable/retractable lip 301 when in the retracted state, as illustrated in FIG. 4B. In one embodiment, the extendable/retractable lip 301 has a notch 402 that may be grasped by a hand or finger of the user 401 to extend the extendable/retractable lip 301 outward from the enclosure apparatus 100. Alternatively, the extendable/retractable lip 301 may be pressure-activated without the notch 402. For example, the extendable/retractable lip 301 may be spring-loaded to extend upon pressure from the hand or finger of the user 401. FIG. 4C illustrates the extendable/retractable lip 301 in the extended state. The user 401 may push the extendable/retractable lip 301 to retract the extendable/retractable lip 301 back into the cavity from which it extended.

Figure 5:
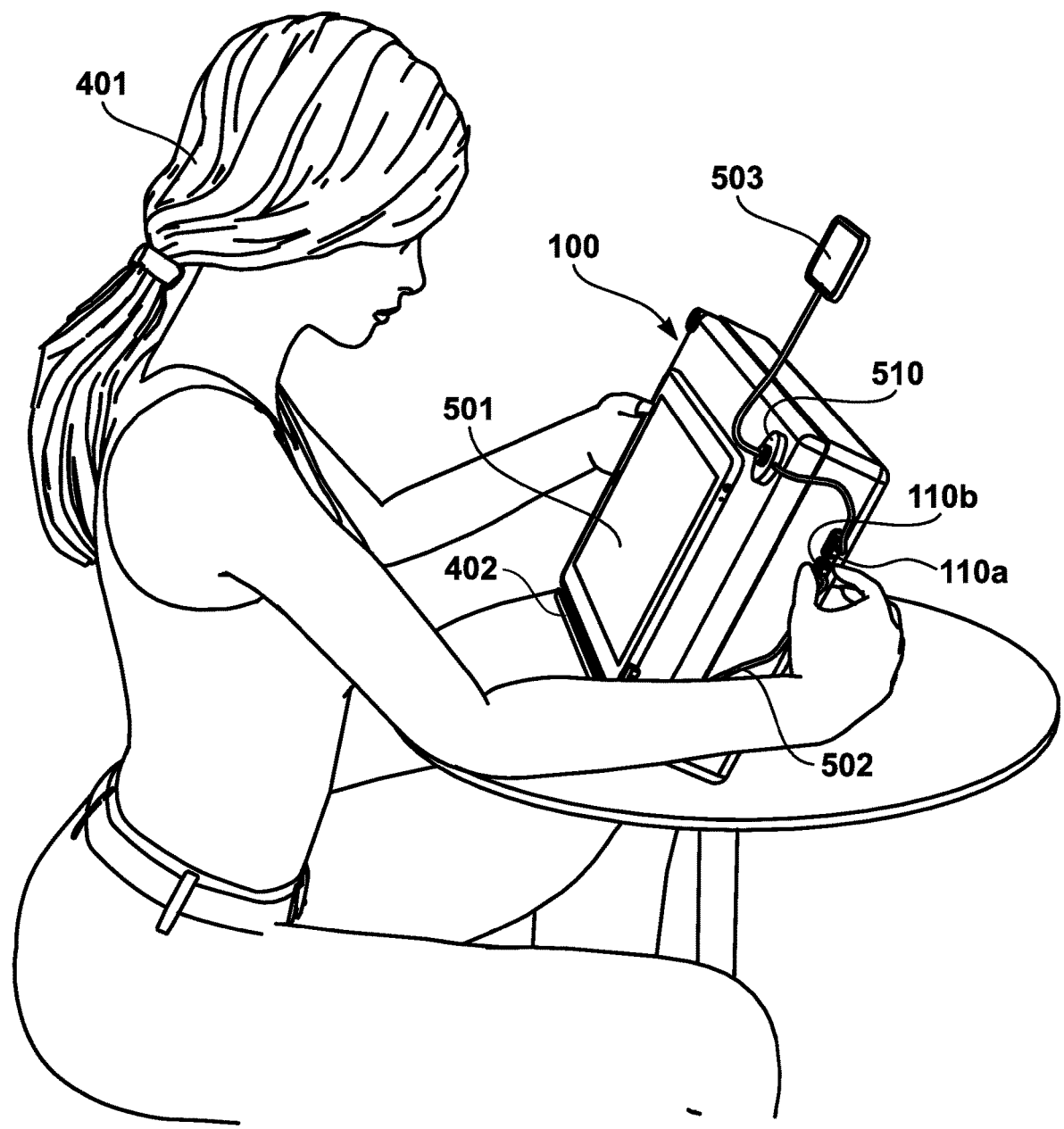
FIG. 5 illustrates the user placing a mobile computing device in the extendable/retractable lip in its extended state.

Moreover, FIG. 5 illustrates the user 401 placing a mobile computing device 501 in the extendable/retractable lip 301 in its extended state. As an example, the mobile computing device 501 is illustrated as being a tablet device. (Other types of mobile computing devices, such as a smartphone, may be utilized instead.) The extendable/retractable lip 301 is configured to extend enough to allow an edge of the mobile computing device 501 to be received, but may also be retracted after insertion to securely fit the mobile computing device 501. For example, if the tablet device is six millimeters thick, the user 401 may extend the extendable/retractable lip 301 eight millimeters to insert the tablet device, and then manually apply pressure to the front of the extendable/retractable lip 301 to retract it to approximately six millimeters to securely fit the tablet device. In one embodiment, the enclosure apparatus 100 may have a locking actuator (e.g., button) that locks the extendable/retractable lip 301 in position. The locking actuator prevents the weight of the mobile computing device from extending the extendable/retractable lip 301 during use of the mobile computing device 501.

The extendable/retractable lip 301 may be a universal receiving mechanism, meaning that it can receive a variety of different types of mobile computing devices of different shapes and sizes. For example, the extendable/retractable lip 301 may have a range of motion of five to eight millimeters to accommodate most tablet devices, which typically have a thickness of approximately five to six millimeters, and most smartphones, which typically have a thickness of approximately seven to eight millimeters.

The user 401 may also connect the mobile computing device 501 to the enclosure apparatus 100 (e.g., via a USB cable 502) to the port 110a or 110b to charge the mobile computing device 501 via the internal power supply 109.

Furthermore, in another embodiment, the enclosure apparatus 100 may store the lighting device 503 that emits light for use with the mobile computing device 100, especially during the evening. Given that the components of the enclosure apparatus 100 may be utilized for skincare rejuvenation, the user 501 may want additional light for viewing his or her skin during use of the skincare rejuvenation system components. The lighting device 503 may be stored within the enclosure apparatus 100 and attached via the attachable base 510 to the enclosure apparatus 100. Alternatively, the lighting device 503 may be attached to the exterior of the enclosure apparatus 100, without temporary storage within the enclosure apparatus 100, and adjusted as needed by the user 401.

Figure 6A:
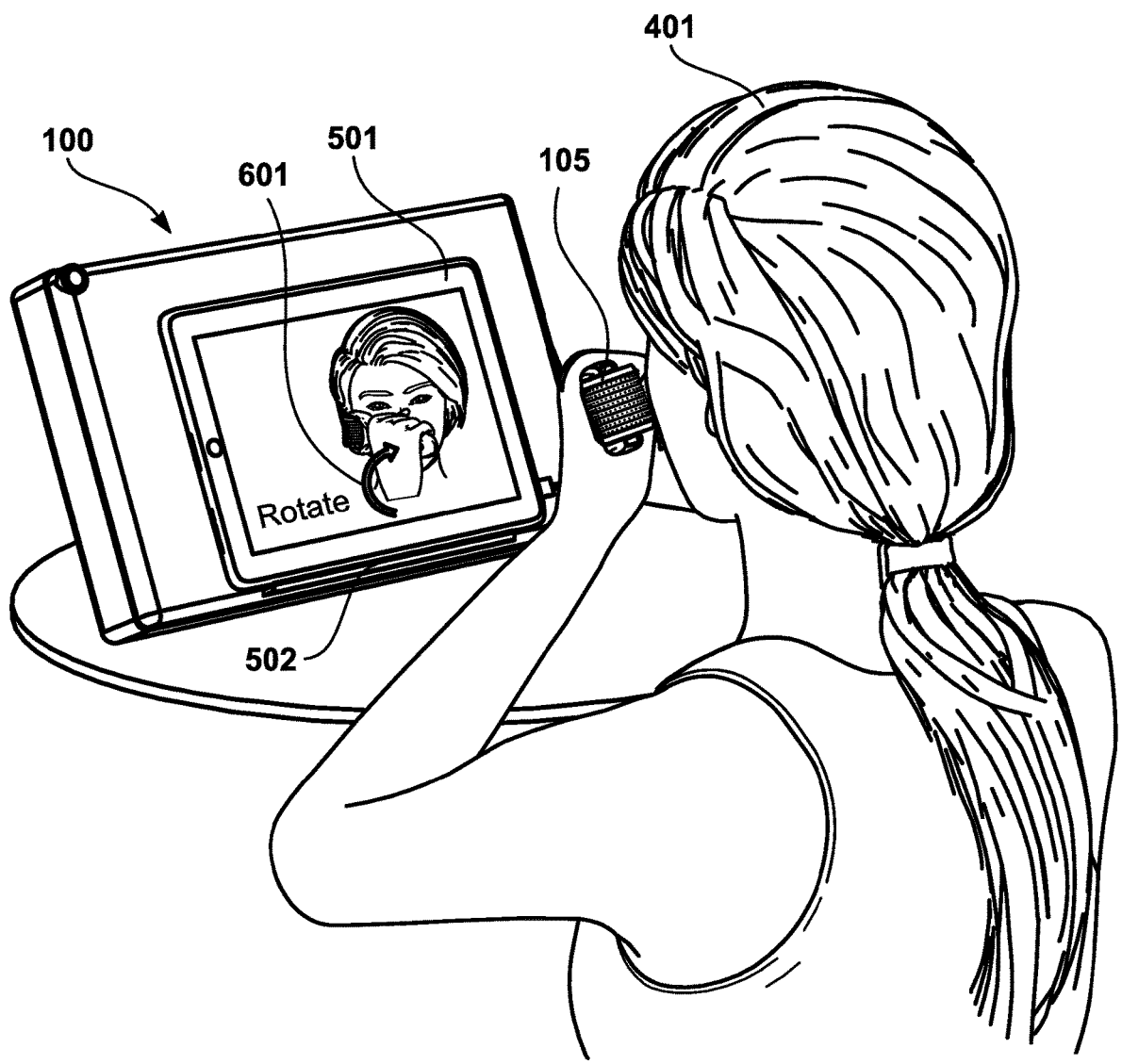
FIG. 6A illustrates the user performing the first step of the three-step process incorrectly, and the app providing one or more virtual cues for the user to perform this step correctly.
Figure 6B:
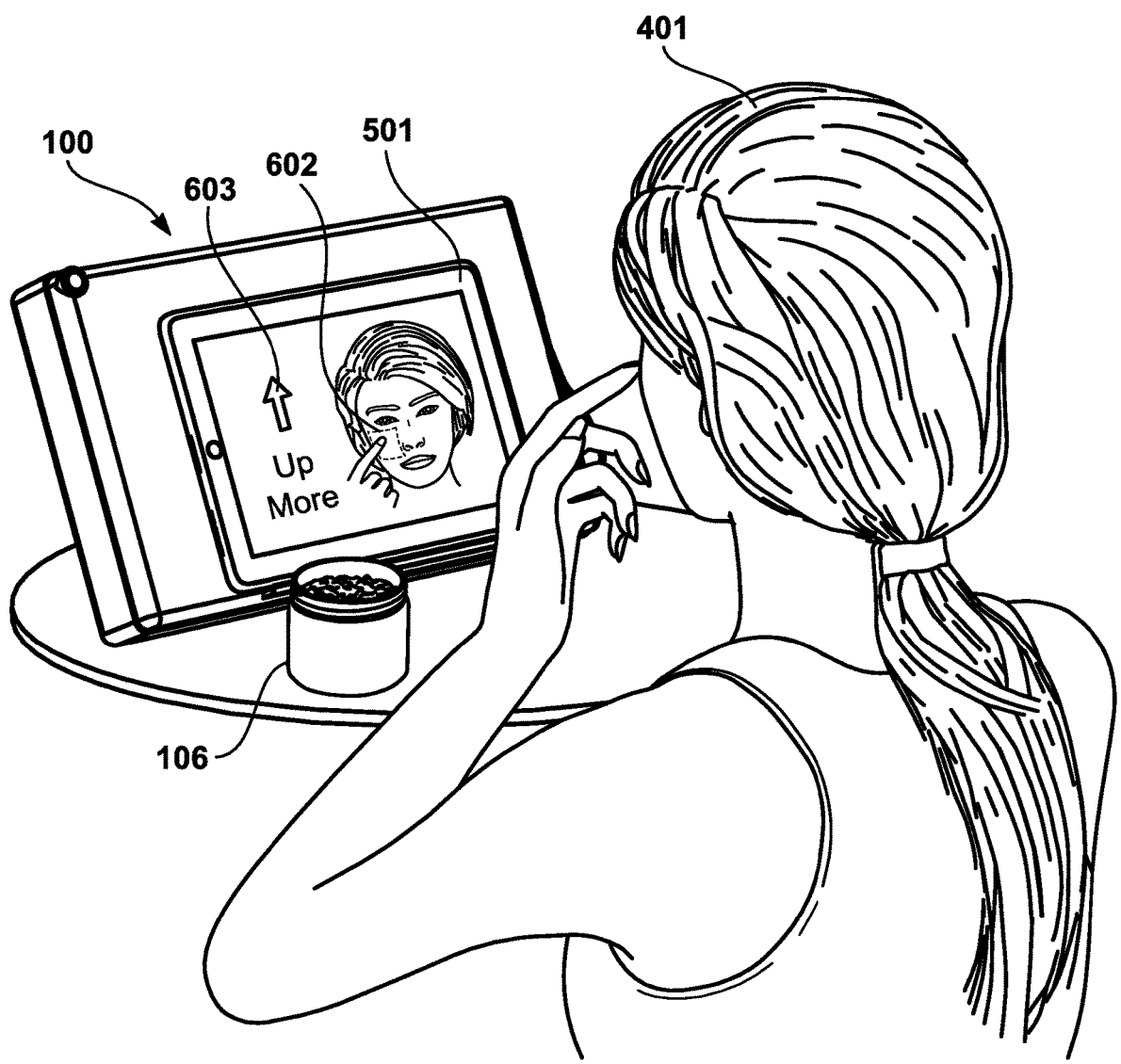
FIG. 6B illustrates the user performing the second step of the three-step process incorrectly.
Figure 6C:
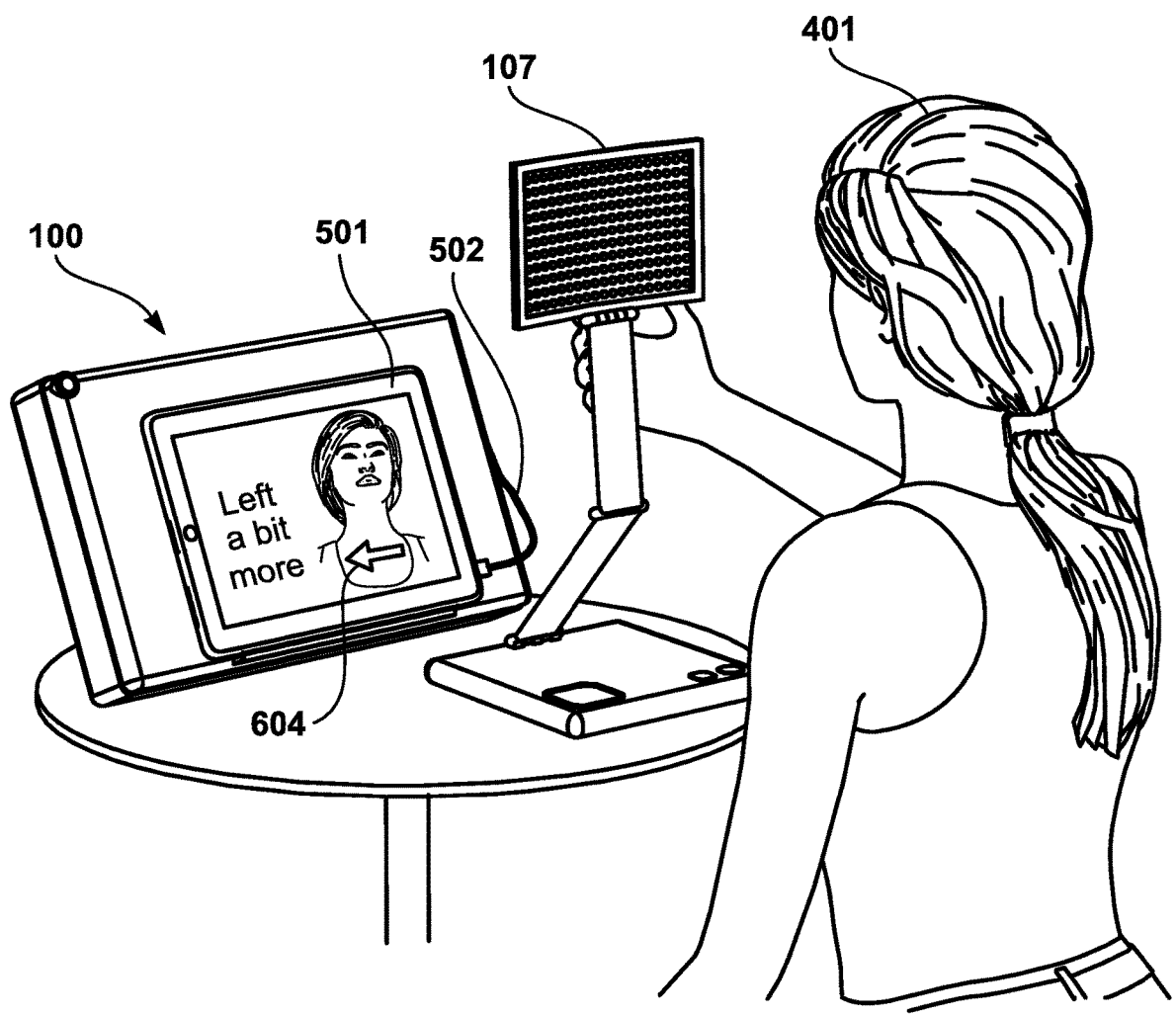
FIG. 6C illustrates the user performing the third step of the three-step process.

After insertion of the mobile computing device 501 into the extendable/retractable lip 301, the user 401 may utilize the mobile computing device 501 to execute an app in conjunction with use of the components that were previously stored within the enclosure apparatus 100. As an example, FIGS. 6A-6C illustrate the user 401 utilizing an app executed by the mobile computing device 501 to perform the aforementioned three-step process with the derma roller 105, the chemical compound 106, and the red light therapy device 107. In particular, FIG. 6A illustrates the user 401 performing the first step of the three-step process incorrectly, and the app providing one or more virtual cues 601 for the user 401 to perform this step correctly. In this example, the user 401 should be moving the derma roller 105 in a vertical motion, but instead is moving it in a horizontal motion. Accordingly, the app rendered by the mobile computing device 501 depicts a virtual cue 601 in the form of an arrow to alert the user 401 to adjust the movement of the derma roller 105. (An arrow is just one example of a visual-based virtual cue. Additionally, or alternatively, audio-based cues may be utilized.) Furthermore, FIG. 6B illustrates the user 401 performing the second step of the three-step process incorrectly. For example, the user 401 may apply the chemical compound 106 outside of a predefined area 602 (e.g., a four inch by four inch patch) that surrounds the intended area of rejuvenation, but that predefined area is an optimal area for skincare rejuvenation. Accordingly, a virtual cue 603 may direct the user 108 to apply the chemical compound within the predefined area 602. Finally, FIG. 6C illustrates the user 401 adjusting a red light therapy emission device 107 in a manner that does not optimally emit red light therapy toward the intended area of rejuvenation. The app generates a virtual cue 604 to direct the user 401 to adjust the red light therapy device 107 to perform optimal emissions toward the user 401.

FIGS. 6A-6C depict just one example of an app for a specific process. The app may be utilized for other skincare rejuvenation processes in conjunction with other components.

It is understood that the processes, systems, and apparatuses described herein may also be applied in other types of processes, systems, and apparatuses. Those skilled in the art will appreciate that the various adaptations and modifications of the embodiments of the processes, systems, and apparatuses described herein may be configured without departing from the scope and spirit of the present processes and systems. Therefore, it is to be understood that, within the scope of the appended claims, the present processes, systems, and apparatuses may be practiced other than as specifically described herein.

I claim:
1. An enclosure apparatus comprising:
a first wall;
a second wall;
a third wall;
a fourth wall;
a bottom portion operably attached to the first wall, the second wall, the third wall, and the fourth wall;
a support mechanism that is operably attached to an exterior surface of the bottom portion, the support mechanism configured to extend outwardly away from the bottom portion to position the enclosure apparatus in an upright position;
a top portion operably attached to the first wall, the second wall, the third wall, and the fourth wall;
a swivel mechanism operably connected to a corner of the top portion and at least one of the first wall, the second wall, the third wall, and the fourth wall, wherein the swivel mechanism rotates the top portion with respect to a remainder of the enclosure apparatus to open and close the enclosure apparatus, wherein the top portion rotates in a plane parallel to a face of the bottom portion, and wherein the swivel mechanism rotates in a plane perpendicular to a face of the top portion; and
a lip mechanism operably attached to an edge of the top portion, the lip mechanism configured to receive a mobile computing device, wherein the lip mechanism is moveable between a retracted position and an extended position, wherein the lip mechanism is disposed against the top portion in a cavity in the retracted position, wherein the lip mechanism is configured to extend away from the top portion and out of the cavity in the extended position to allow an edge of the mobile computing device to be received, and wherein the lip mechanism is configured to retract after the mobile computing device is received by the lip mechanism so as to securely fit the mobile computing device between the lip mechanism and the top portion.

2. The enclosure apparatus of claim 1, further comprising a power supply compartment within an interior portion of the enclosure apparatus, the power supply compartment storing a rechargeable power supply.

3. The enclosure apparatus of claim 2, further comprising a port for supplying power to the mobile computing device via a cable connected to the mobile computing device, the port being positioned on an exterior portion of the enclosure apparatus.

4. The enclosure apparatus of claim 1, wherein the lip mechanism comprises a notch configured to be grasped by a finger of a user to extend the lip mechanism outward from the top portion.

5. The enclosure apparatus of claim 1, wherein the lip mechanism is spring-loaded such that the lip mechanism is configured to retract toward the enclosure apparatus to secure positioning of the mobile computing device.

6. The enclosure apparatus of claim 1, wherein the support mechanism comprises a support member that is operably attached to one or more hinges, the one or more hinges being operably attached to the bottom portion.

7. The enclosure apparatus of claim 1, further comprising one or more magnets, wherein the one or more magnets secure the mobile computing device to the top portion when the mobile computing device is received in the lip mechanism.

8. The enclosure apparatus of claim 6, wherein the lip mechanism is positioned along an edge of the top portion that is parallel with the one or more hinges, and wherein the lip mechanism is positioned below the one or more hinges such that the lip mechanism is configured to bear a weight of the mobile computing device without any additional attachment mechanism.

9. The enclosure apparatus of claim 6, wherein the enclosure apparatus further comprises an adjustment member that is configured to adjust the angle at which the enclosure apparatus is positioned upright, wherein the adjustment member comprises one or more adjustment protrusions that interface with the support mechanism to adjust the angle at which the enclosure apparatus is positioned upright.

10. The enclosure apparatus of claim 1, wherein the lip mechanism has a range of motion of five to eight millimeters to accommodate the mobile computing device.

11. The enclosure apparatus of claim 1, further comprising one or more skincare rejuvenation components of a skincare rejuvenation system, the one or more skincare rejuvenation components being stored within an interior portion of the enclosure apparatus, wherein the interior portion of the enclosure comprises form fitting molded to correspond to specific shapes of at least one of the one or more skincare rejuvenation components.

12. The enclosure apparatus of claim 1, further comprising a locking actuator, wherein the locking actuator locks the lip mechanism in position such that a weight of the mobile computing device does not extend the lip mechanism during use of the mobile computing device.

13. An enclosure apparatus comprising:
a first wall;
a second wall;
a third wall;
a fourth wall;
a bottom portion operably attached to the first wall, the second wall, the third wall, and the fourth wall;
a support mechanism that is operably attached to an exterior surface of the bottom portion, the support mechanism configured to extend outwardly away from the bottom portion to position the enclosure apparatus in an upright position;
a top portion operably attached to the first wall, the second wall, the third wall, and the fourth wall;
a swivel mechanism operably connected to a corner of the top portion and at least one of the first wall, the second wall, the third wall, and the fourth wall, wherein the swivel mechanism rotates the top portion with respect to a remainder of the enclosure apparatus to open and close the enclosure apparatus, wherein the top portion rotates in a plane parallel to a face of the bottom portion, and wherein the swivel mechanism rotates in a plane perpendicular to a face of the top portion;
a lip mechanism operably attached to an edge of the top portion, the lip mechanism configured to receive a mobile computing device, wherein the lip mechanism is moveable between a retracted position and an extended position, wherein the lip mechanism is disposed against the top portion in a cavity in the retracted position, wherein the lip mechanism is configured to extend away from the top portion and out of the cavity in the extended position to allow an edge of the mobile computing device to be received, and wherein the lip mechanism is configured to retract after the mobile computing device is received by the lip mechanism so as to securely fit the mobile computing device between the lip mechanism and the top portion; and
a power supply compartment within an interior portion of the enclosure apparatus, the power supply compartment storing a rechargeable power supply; and
a port for supplying power to the mobile computing device via a cable connected to the mobile computing device, the port being positioned on an exterior portion of the enclosure apparatus.

14. The enclosure apparatus of claim 13, further comprising:
a form fitting molded to correspond to specific shapes of at least one of one or more skincare rejuvenation components of a skincare rejuvenation system, the one or more skincare rejuvenation components being stored within the interior portion of the enclosure apparatus.

15. The enclosure apparatus of claim 13, wherein the lip mechanism comprises a notch configured to be grasped by a finger of a user to extend the lip mechanism outward from the top portion.

16. The enclosure apparatus of claim 13, further comprising one or more magnets, wherein the one or more magnets secure the mobile computing device to the top portion when the mobile computing device is received in the lip mechanism.

17. The enclosure apparatus of claim 13, wherein the lip mechanism is spring-loaded such that the lip mechanism is configured to retract toward the enclosure apparatus to secure positioning of the mobile computing device.

18. The enclosure apparatus of claim 13, further comprising a locking actuator, wherein the locking actuator locks the lip mechanism in position such that a weight of the mobile computing device does not extend the lip mechanism during use of the mobile computing device.

19. The enclosure apparatus of claim 13, wherein the one or more hinges are positioned in substantial proximity to a midline of the bottom portion.

20. The enclosure apparatus of claim 19, wherein the lip mechanism is positioned along an edge of the top portion that is parallel with the one or more hinges, and wherein the lip mechanism is positioned below the one or more hinges such that the lip mechanism is configured to bear a weight of the mobile computing device without any additional attachment mechanism.

* * * * *